United States Patent

Fan et al.

Patent Number: 5,075,556
Date of Patent: Dec. 24, 1991

[54] ACRIDINE ORANGE DERIVATIVES AND THEIR USE IN THE QUANTITATION OF RETICULOCYTES IN WHOLE BLOOD

[75] Inventors: Sophie Fan, Millwood, N.Y.; Gena Fischer, Harrington Park, N.J.

[73] Assignee: Technicon Instruments Corporation, Tarrytown, N.Y.

[21] Appl. No.: 444,255

[22] Filed: Dec. 1, 1989

[51] Int. Cl.$^5$ .................. C07D 219/08; G01N 21/64; G01N 33/52

[52] U.S. Cl. .................. 250/459; 250/461.2; 424/7.1; 436/63; 436/96; 436/172; 436/520; 514/452; 546/107

[58] Field of Search .................. 250/461.2, 459.1; 546/107; 424/7.1; 436/172, 63, 96, 520

[56] References Cited

U.S. PATENT DOCUMENTS 4,336,029 6/1982 Natale .................. 250/461.2

OTHER PUBLICATIONS

Erbrich et al., Chem. Abstract, vol. 96:19937g (1981).
Albert, A., *The Acridines*, 2nd Ed. (1966), New York, p. 534.

*Primary Examiner*—Donald G. Daus
*Assistant Examiner*—Philip I. Datlow
*Attorney, Agent, or Firm*—Jeffrey M. Greenman

[57] ABSTRACT

Quaternized derivatives of acridine orange and reagents incorporating such derivatives and their use in quantitatively determining reticulocyte levels in whole blood specimen by fluorescence flow cytometry techniques are disclosed. The quaternized derivatives of acridine orange are of the general formula:

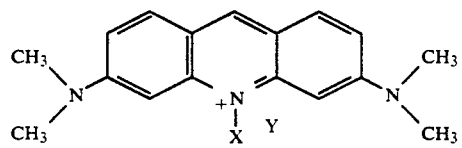

wherein
Y is bromide (Br$^-$) or iodide (I$^-$), and
X may be R$_1$ and/or R$_2$ substituted benzyl group

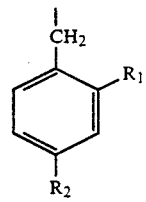

R$_1$ is hydrogen or fluorine, and R$_2$ is fluorine, trifluoromethyl or hydrogen, or X may be hydroxyl ethylene.

15 Claims, 16 Drawing Sheets

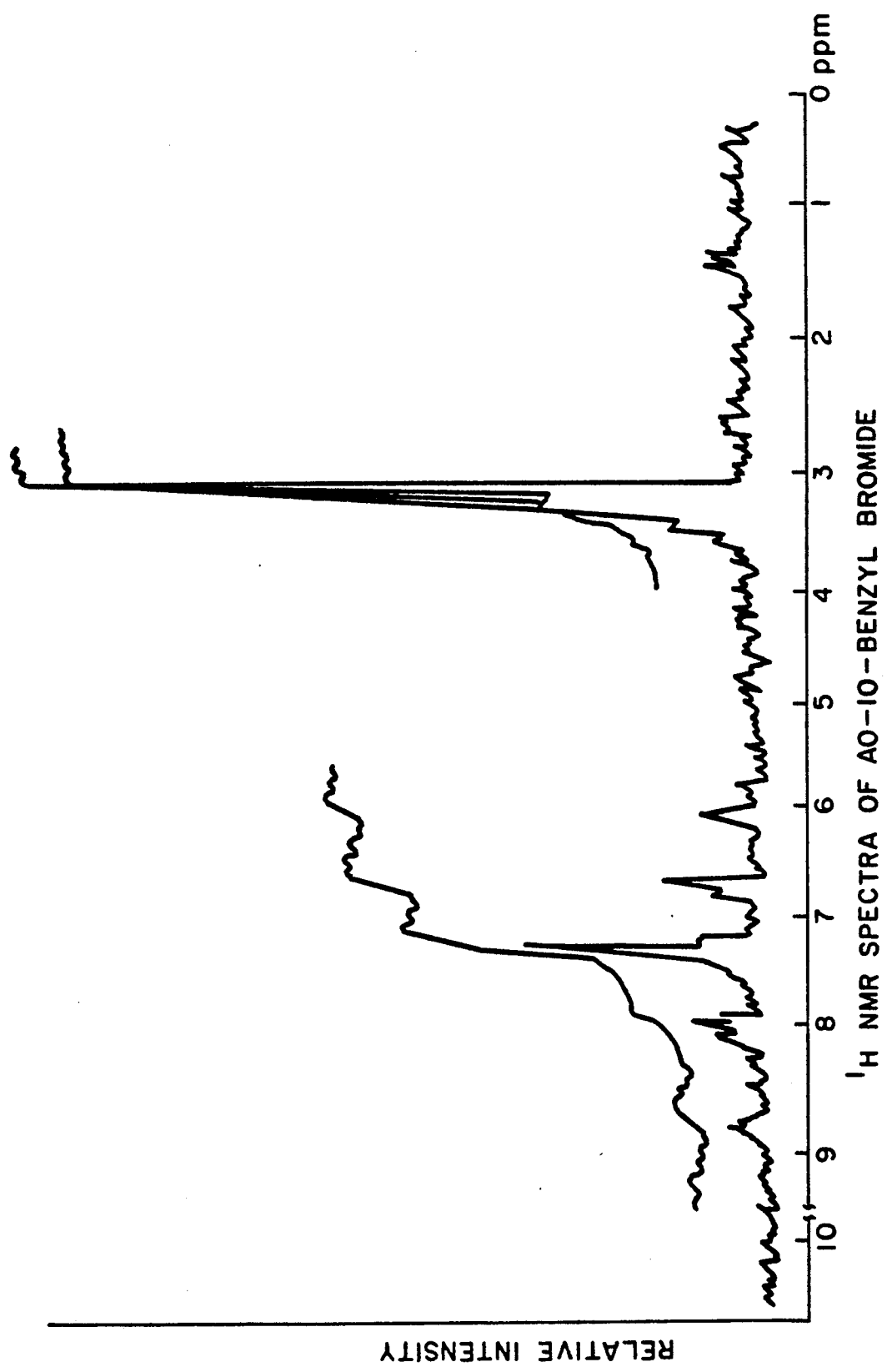

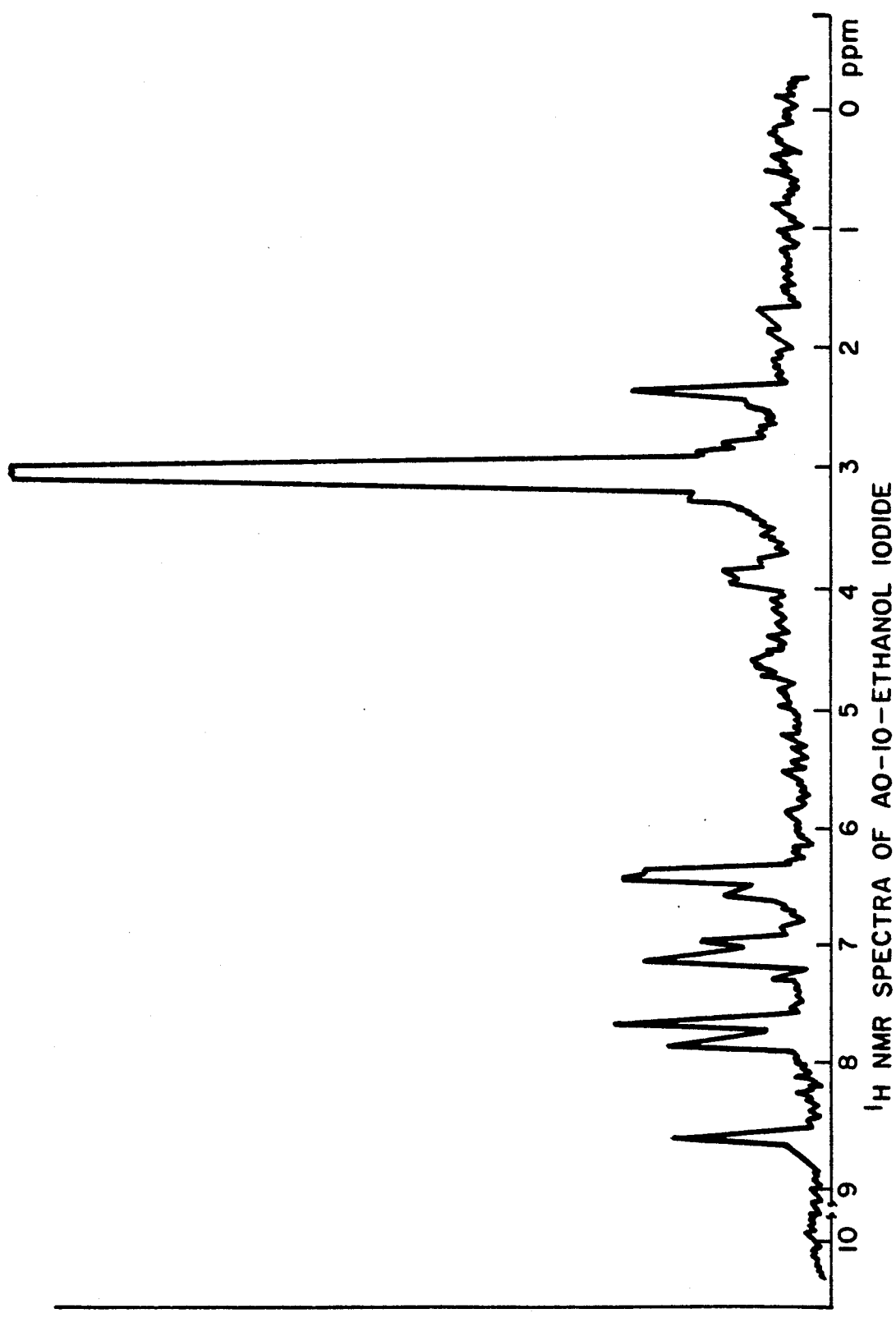

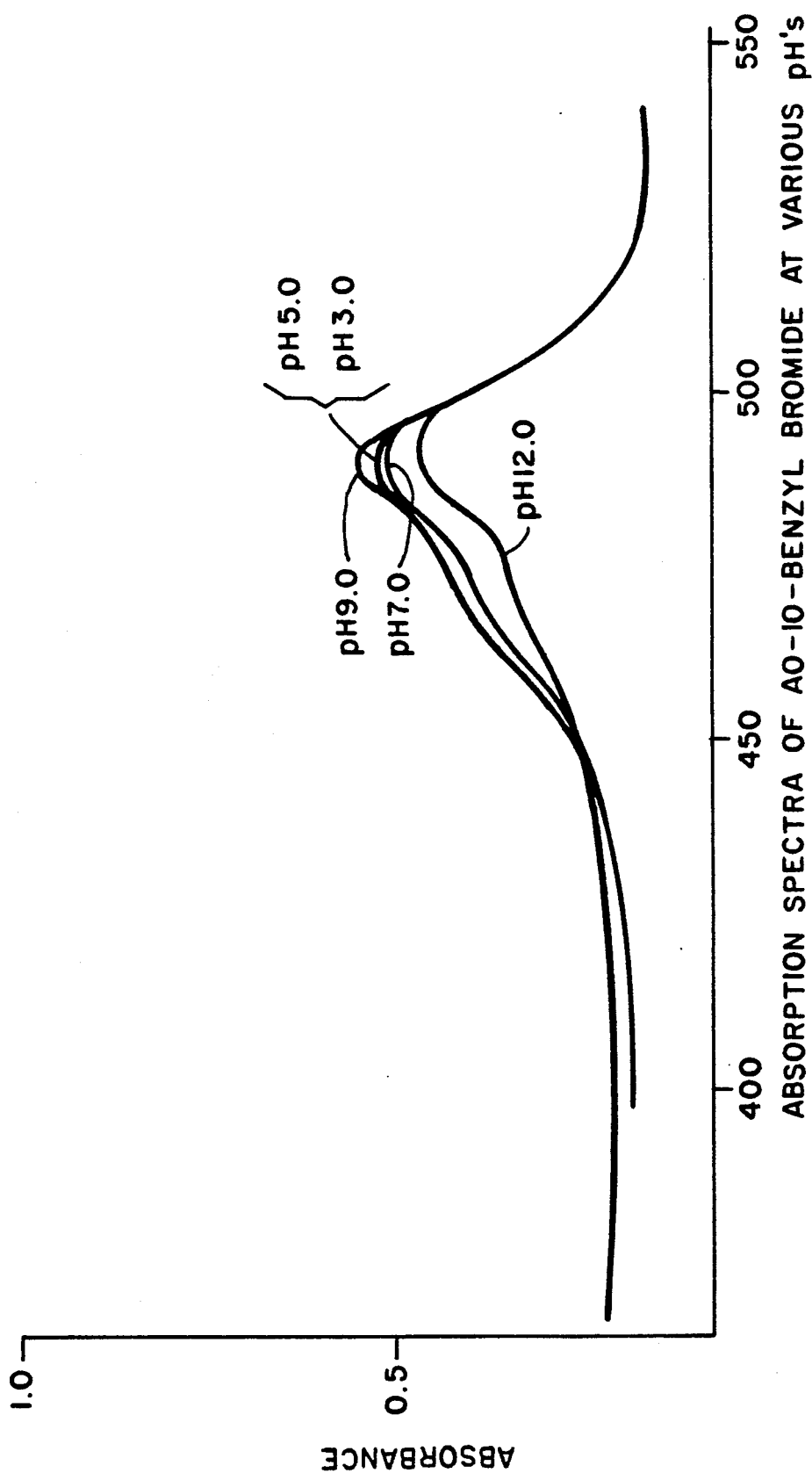

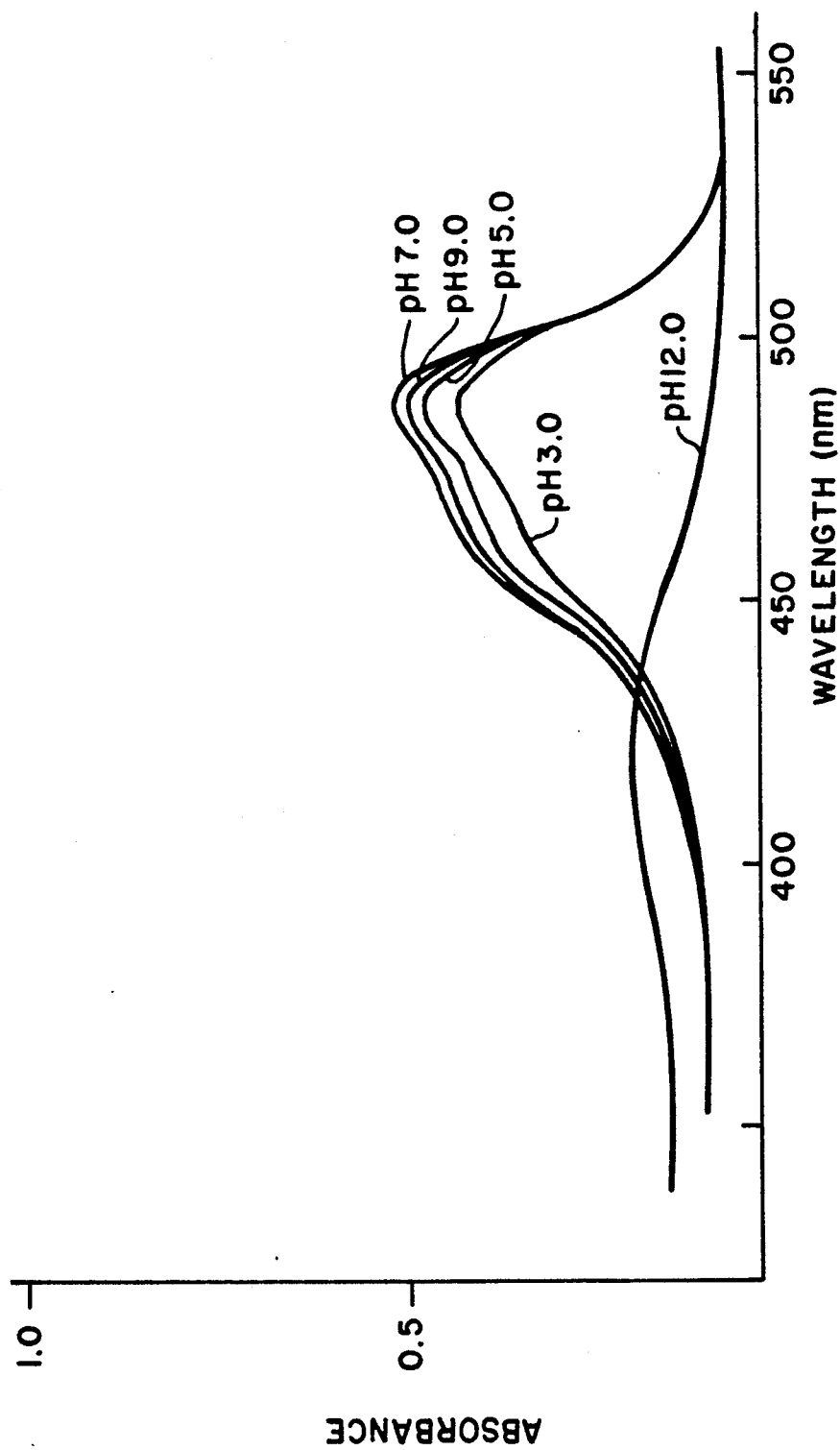

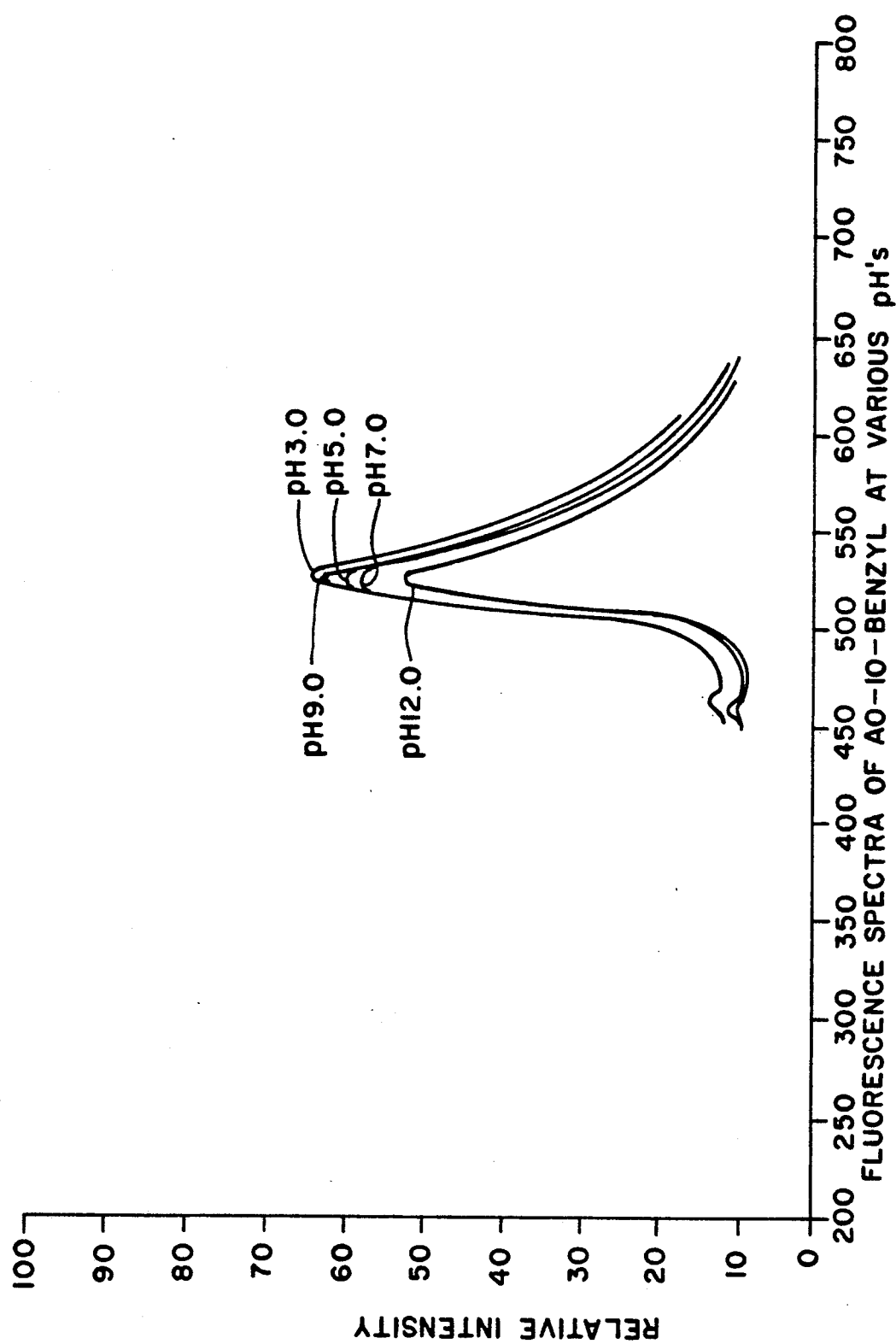

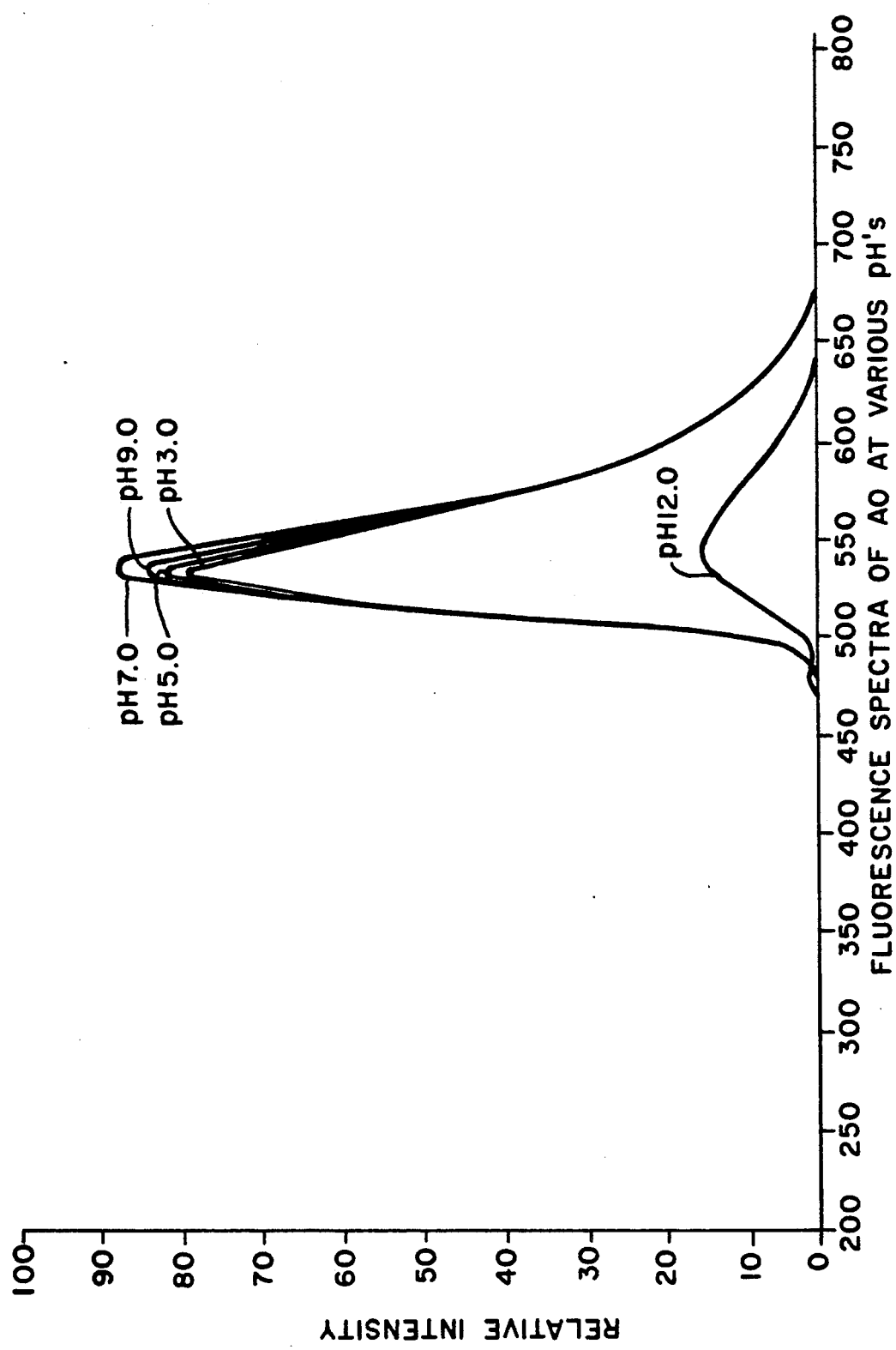

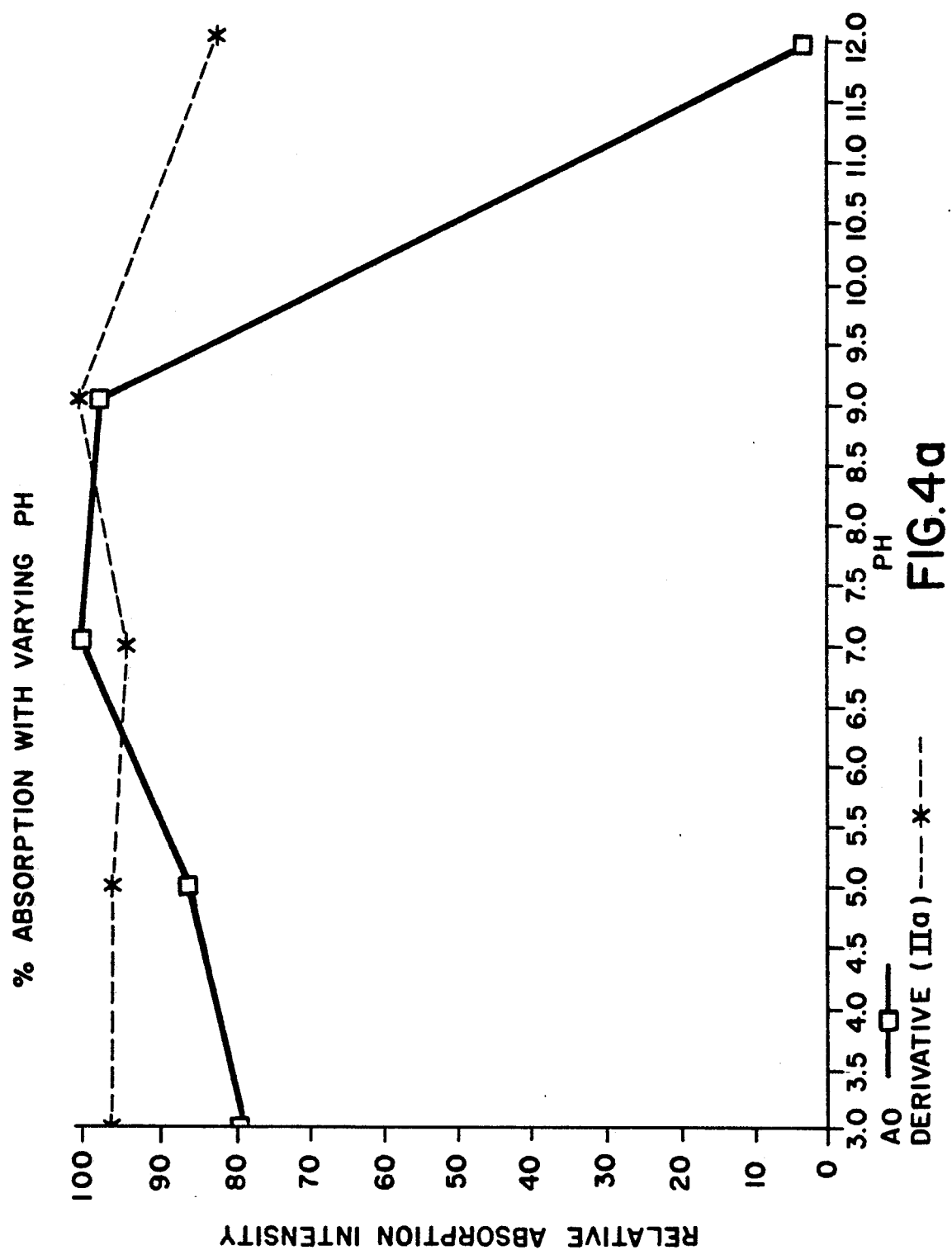

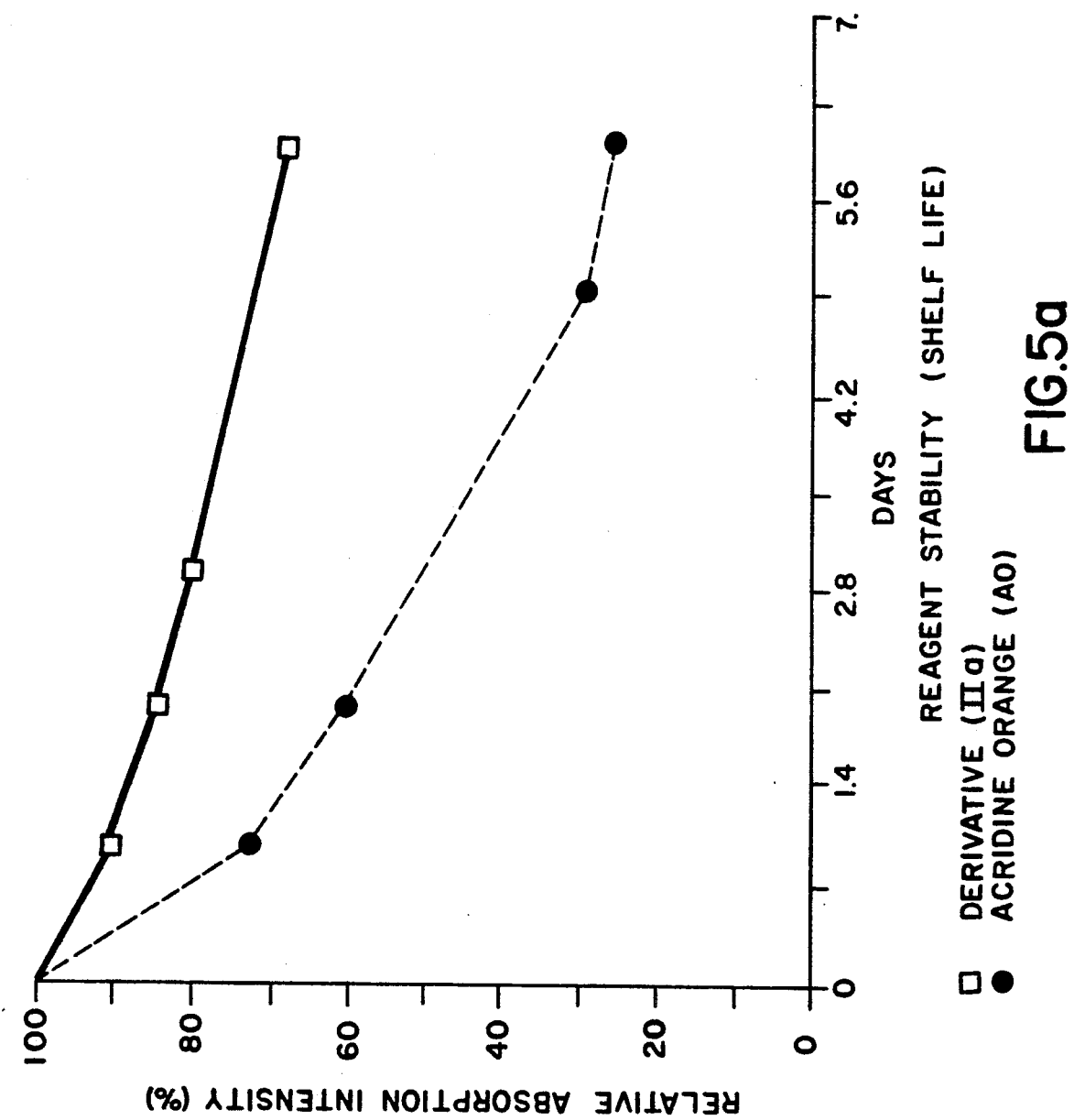

REGRESSION LINE
NUMBER OF SAMPLES = 43  MEAN X = 3.218837
MEAN Y = 2.78  ST. DEV. OF X = 3.365184
ST. DEV. OF Y = 3.018095  SLOPE = 0.868529
INTERCEPT = −0.015653  S.D. OF SLOPE = 0.034926
S.D. OF INTERCEPT = 0.161652  CORR. COEFF. = 0.968412
S.D. OF REGRESSION = 0.761702

ACRIDINE ORANGE DERIVATIVES AND THEIR USE IN THE QUANTITATION OF RETICULOCYTES IN WHOLE BLOOD

BACKGROUND OF THE INVENTION

1. Field of the Invention

The present invention relates to compounds and reagents for enumerating cells in samples of whole blood and more particularly to quaternized derivatives of acridine orange and reagents incorporating such derivatives and their use in quantitatively determining reticulocyte levels in a whole blood specimen by fluorescence flow cytometry techniques.

2. Description of the Prior Art

In all the higher animals, blood consists of an aqueous fluid part (the plasma) in which are suspended corpuscles of various kinds: the red blood cells (erythrocytes), the white blood cells (leukocytes) and the blood platelets. Plasma has a composition comprising roughly 90% water, 9% protein, 0.9% salts and traces of other materials such as sugar, urea, uric acid and the like.

The cells or corpuscles of the peripheral blood (i.e. the blood outside the bone marrow) are divided into two main groups: the red blood cells (erythrocytes), whose primary object is to transport oxygen, and the white blood cells (leukocytes), whose primary functions relate to the immune system and the destruction of materials foreign to the body. In addition to these two main groups, the blood also contains the so-called blood platelets which are important in hemostatis.

The final stages of erythrocyte maturation occur after their release from the bone marrow while these cells are circulating in the peripheral blood. These young red cells, or "reticulocytes", have lost their nucleus and thus their ability to divide or to synthesize RNA. Although these functions have ceased, reticulocytes are still metabolically active and are capable of synthesizing protein, taking up iron for the synthesis of heme, and carrying out the necessary metabolic reactions required to maintain an energy rich state. These cells are usually distinguished from mature erythrocytes through the presence of the reticulum which give them their name. This reticulum may be dyed by such agents as brilliant cresyl blue, nile blue sulfate or new methylene blue after which quantitation of reticulocytes may be performed by way of manual observation under a microscope.

Although reticulocytes normally comprise about 0.5 to 2 percent of the total red blood cell population, this percentage can change dramatically under abnormal conditions. For example, reticulocyte counts have been used for many years as a diagnostic aid in studying blood dyscrasias and as an index of red cell regeneration following hemorrhage, as well as for monitoring early toxicity in chemotherapy of certain malignant diseases.

The use of fluorescing stains or dyes for analysis of blood cells has ben known for many years. Particularly, the utilization of acridine orange as a fluorescent dye to stain nucleic acid has been known for over forty years. S. Strugger, *Fluorescence Microscope In Examination Of Bacteria In Soil*. Canad J. Res. C 26: 188–193 (1948) J. B. Vander, et al., J. Lab. Clin. Med 62, 132 (1963) described the use of acridine orange for the identification of reticulocytes by fluorescence microscopy. However, this technique required visual examination of the sample and thus possessed the inherent disadvantages of such manual optical examination methods.

A quaternized acridine orange derivative and its interaction with DNA ar discussed in *In Vitro Effects Of Acridine Interaction On RNA Polymerase Interactions With Supercoiled DNA*, Robert S. Greene, et al., It. J. Biochem., Vol. 15, No. 10, pps. 1231–1239 (1983). A study as performed of the interactions of homologous *E. coli* RNA polymerase with a recombinant plasmid containing the origin sequence of the *E. coli* chromosome. These interactions were analyzed by perturbation of the DNA template, i.e. extracellular DNA, and its supercoiled conformation with the intercalating dye acridine orange and an N-10-benzyl derivative of acridine orange. Characterization of the drug mediated perturbations of the enzyme DNA interactions were accomplished by kinetic, electrophoretic and autoradiographic methods under conditions specific for RNA polymerase-template binding, initiation and transcription. Based on these studies, the authors concluded that acridine orange interfered with the RNA polymerase-DNA template interaction much more efficiently than the N-10-benzyl substituted acridine orange. In effect, the authors found that acridine orange was a more effective DNA intercalator than the acridine orange derivative. There is no discussion that the specific acridine orange derivative could be used as a dye for cell analysis using fluorescence flow cytometry or as an intercellular RNA marker in general.

Additionally, many different types of automatic apparatus have been disclosed for detecting and quantitating blood cells. Representative of such methods (some of which use acridine orange or other fluorescent dyes) are U.S. Pat. No(s). 3,497,690, 3,916,205, 3,864,171 and 4,027,971. While these references generally disclose the us of fluorescent dyes in a variety of apparatus, including a flow cytometer, they do not provide a method or composition for quantitating reticulocytes by fluorescence.

Of particular interest are Adams and Kamentsky U.S. Pat. No. 3,684,377 and Adams U.S. Pat. No. 3,883,247. These patents relate to method and dye compositions for quantitating cells (particularly white blood cells) using a metachromatic fluorochrome dye such as acridine orange.

The Adams and Kamentsky patent describes the use of a vital dye composition for differential blood analysis of living white cells which consist essentially of acridine orange having a concentration between $10^{-7}$ and $10^{-5}$ grams per ml, the acridine orange solution having a pH factor and an osmolality within the normal physiological ranges for human blood plasma. While the patent teaches that this composition is useful for identifying the various types of white blood cells and for distinguishing them from other bodies in the blood, there is no teaching that this composition has any use in the enumeration of reticulocytes.

The Adams patent represents a modification of the teaching of Adams and Kamentsky in that the white blood cells are treated under conditions in which the cells are "shocked" by exposure to a non-physiologic medium during staining. That is, the staining composition used in the Adams patent is made hypotonic, the osmolality thereof being generally below that normally found in human blood. The teaching of the Adams patent is that this hypotonic condition produces a differential rate of uptake of acridine orange dye by the various types of white blood cells, thus allowing them to be more clearly distinguished from one another than in previous techniques. Although the Adams patent does purport to disclose a method for the detection of reticulocytes, the method disclosed therein has been criticized as being practically useless for the quantitation of reticulocytes in Natale U.S. Pat. No. 4,336,029.

In contrast to the Adams and Kamentsky and the Adams patents in which the differentiation of the subtypes of white blood cells depends upon the rate of uptake of the acridine orange dye, the invention of the Natale patent depends upon removing the kinetic factors and increasing the degree of dye uptake so that the reticulocytes will absorb a maximum amount of acridine orange dye. With prior art staining reagents, the reticulocytes absorb only small amounts of dye and therefore yield only low levels of fluorescence in any fluorescence detecting method. These low levels of fluorescence could generally not be well detected over the background fluorescence and consequently only a portion of reticulocytes in the sample could be detected The dye composition of the Natale patent consists essentially of an aqueous solution of the metachromatic fluorochrome dye acridine orange, a chelating agent (citrate), an amino-group reacting reagent, and (if needed) an buffer to maintain the final pH of this solution at approximately 7.4. The osmolality of the solution is maintained at approximately 0.26 osmolality units, the normal physiological level, either by the chelating agent or by addition of sodium chloride as required. The main purpose of the Natale teaching is to identify both reticulocytes and platelets simultaneously. In fact, the Natale reagent contains citrate ions to maximize platelet staining.

The Natale reagent contains very high concentrations of the acridine orange dye ($10^{-2}$ gram per liter) which has been found to stain the fluid conduits within the instrument, including the flow cells, resulting in false positive readings for white cells. This staining also creates carryover problems requiring extensive washing of the system which adds time consuming steps to the assay protocol.

Furthermore, the prior art disclosures regarding acridine orange specifically taught against having maximum acridine orange uptake, since such maximum uptake would destroy the discrimination among the various subclasses of white blood cells which was the main object of these prior art methods. Therefore, the prior art Adams and Adams and Kamentsky patents cannot be said to teach the subject composition or method.

Accordingly, there exists a need for improved acridine orange dyes and reagents useful for the quantitation of reticulocytes by fluorescence flow cytometry techniques. It is a principal object of the present invention to provide such dyes and reagents.

SUMMARY OF THE INVENTION

The present invention provides improved dye compositions and reagents incorporating such compositions for the quantitative determination of reticulocytes in whole blood.

The dye of the present invention consists of special structures of quaternized derivatives of acridine orange which have proven to be more stable chemically and provide greater reproducibility of reticulocyte counts when compared to dyes used previously. The quaternized acridine orange derivatives of the present invention have the following general formula (I):

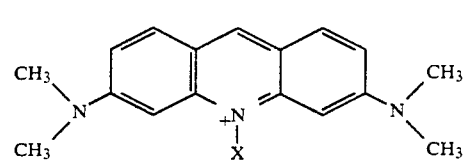

In the above formula, Y may be bromide ($Br^-$) or iodide ($I^-$), and X may be $R_1$ and/or $R_2$ substituted benzyl group,

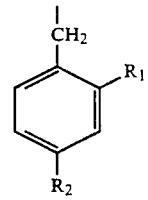

wherein $R_1$ can be either hydrogen or fluorine, and $R_2$ is fluorine, trifluoromethyl ($CF_3$) or hydrogen to form the compound of the general formula (II).

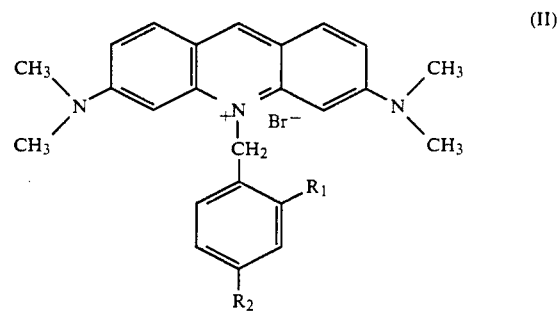

Alternatively, X may be hydroxyl ethylene [$(CH_2)_2OH$] group to form the compound of the general formula (III)

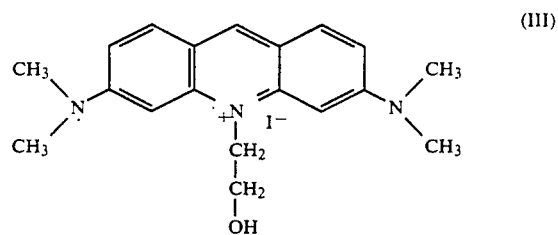

The reagent of the present invention includes the dye compositions of the general formulae (II) and (III) in a novel buffer. Specifically, the reagent comprises 3–9 μg/ml of the subject derivative dye composition in a buffer solution comprising 1.25 g/l paraformaldehyde and 9 g/l potassium oxalate.

The reagent including the subject derivative dye composition may be used to enumerate reticulocytes in a whole blood specimen using the technique of flow cytometry. The fundamental concept of flow cytometry is essentially the passing of cells, one at a time, through a specific sensing region. By means of hydrodynamic focusing, single cells are passed through the sensing zone, which consists of a focused laser light source and a detection system for the measurement of scattered and fluorescent light.

Accordingly, the subject method in its broadest application comprises the steps of:
(a) mixing a sample of blood to be tested with the subject reagent composition including the subject derivative dye composition to form a suspension;
(b) allowing the suspension to react at room temperature for a short time interval, for example, three minutes or less, so that the acridine orange dye is maximally taken up by the reticulocytes;
(c) exposing the suspension to radiation from a blue laser light source;
(d) measuring the intensity of red fluorescence from the suspension; and
(e) determining the amount or percentage of reticulocytes in the sample from said measurements.

DESCRIPTION OF THE DRAWINGS

The above and other objects and significant advantages of the present invention are believed made clear by the following detailed description thereof taken in conjunction with the accompanying drawings wherein:

FIGS. 1a and 1b are the $^1$H NMR spectra of two derivative dyes (IIa and III) of the present invention;

FIGS. 2a and 2b are the absorption spectra of Derivative (IIa) of the present invention and acridine orange respectively;

FIGS. 3a and 3b are the fluorescence spectra of Derivative (IIa) of the present invention and acridine orange respectively;

FIGS. 4a and 4b are pH titration curves for Derivatives (IIa), (IIb) and (III).

FIGS. 5a and 5b illustrate the reagent stability (absorption intensity and fluorescence intensity, respectively) of Derivative (IIa) of the present invention;

DETAILED DESCRIPTION OF THE INVENTION

Figure 4B:
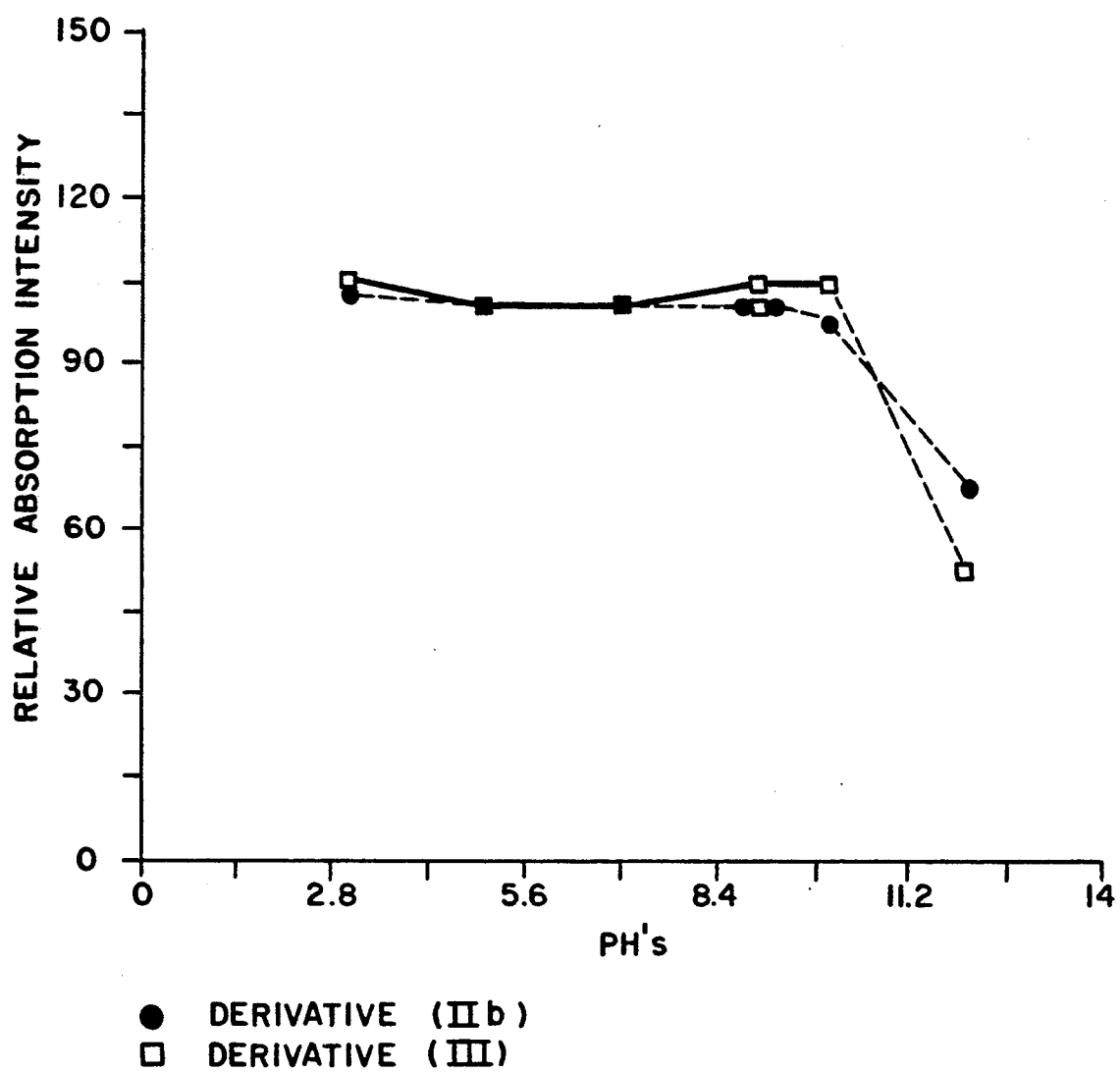

We have found that the special groups of quaternized derivatives of acridine orange disclosed herein are more stable chemically and provide greater reproducibility of reticulocyte counts as compared to methods and dyes used previously. In addition, due to the polar nature of the special groups, these derivatives penetrate the cell membrane of the erythrocytes rapidly and bind to the intracellular RNA specifically such that lower dye concentrations are required for reticulocyte staining and the problems of instrument conduit staining are reduced substantially.

The following examples set forth the synthetic steps of producing the quaternized derivatives of acridine orange of our invention and reagents and methods incorporating the same for quantitating reticulocytes using fluorescence flow cytometry techniques. Standard commercially available reagent grade materials were used whenever possible. It will be understood that the formulations and the procedures which follow are provided for purpose of illustration only and that other ingredients, proportions and procedures can be employed in accordance with the disclosures of this invention.

EXAMPLE 1

Synthesis of 3,6-bis(dimethylamino)10-benzylacridinum bromide

Weigh 0.514 g (or $1.45 \times 10^{-3}$ mole) of acridine orange base

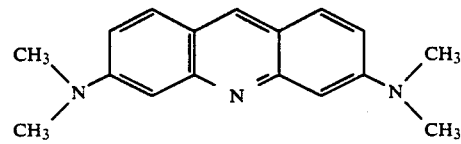

into a two-necked 100 ml round bottom flask equipped with a stirring bar and a reflux condenser. To this flask was added 10 ml of dry toluene (freshly opened toluene dried over sodium spheres). An alkylation agent, pure benzyl bromide, with a total volume of 0.173 ml (or $1.45 \times 10^{-3}$ mole), was slowly added to the stirred mixture in the flask while the mixture was gently heated to 100°–110° C. overnight. Care was taken to keep the temperature below the boiling point of toluene, 111° C. The mixture was cooled to room temperature and the solid precipitate collected with a fitted disc funnel. The solid cake was rinsed thoroughly with toluene and air dried under vacuum. A brick red solid material (approx. 0.381 g) was obtained. Part of the crude product (about 0.27 g) was purified with flash chromatography (18.5 g silica used with $CHCl_3/MeOH/H_2O = 7.5/2.5/0.3$ mol ratio as diluting solvent). About 0.18 g of the purified compound of the following formula was obtained.

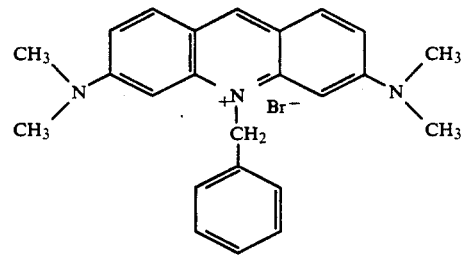

EXAMPLE 2

Synthesis of 3,6-bis(dimethylamino)10-N-benzyl acridinum derivatives

The procedure of Example 1 was followed, with different alkylation agents used at the same molar concentration. Fluorinated benzyl groups were substituted at either the 2 or 4 benzene hydrogens. The alkylation agents included the following:

2-fluoro-benzyl bromide
4-fluoro-benzyl bromide
4-trifluoro-methyl-benzyle bromide A compound of the general formula (II) was obtained:

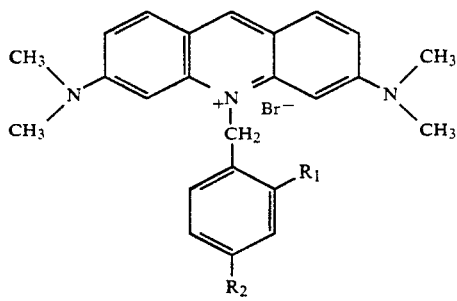

wherein R may be fluorine or hydrogen and $R_2$ is fluorine, trifluoromethyl ($CF_3$), or hydrogen. In the following examples, compounds of this general formula are referred to as the Derivative (II) Family and specific derivatives individually as Derivative (IIa), (IIb), (IIc) or (IId) as follows:

Derivative (IIa), AO-10-Benzyl, wherein $R_1 = R_2 = H$

Derivative (IIb), AO-10-(2F)-Benzyl, wherein $R_1 = F$; $R_2 = H$

Derivative (IIc), AO-10-(4F)-Benzyl, wherein $R_1 = H$; $R_2 = F$

Derivative (IId), AO-10-(4CF$_3$)-Benzyl, wherein $R_1 = H$; $R_2 = CF_3$

EXAMPLE 3;

Synthesis of 3,6-bis(dimethylamino)-10-ethanol acridinum derivative.

In a two-necked 100 ml round bottom flask was weighted 0.508 g acridine orange base. Dry toluene (5 ml) and dimethyl formamide (2 ml) were added to the flask which was equipped with a reflux condenser and a pressure equalizing funnel. 2-iodoethanol (0.261 g dissolved in 5 ml toluene) was added dropwise to the mixture which was constantly stirred and heated at about 110° C. The addition process of 2-iodoethanol took place in about one hour. The reaction was allowed to proceed with reflux overnight. The reflux mixture was then cooled to room temperature. Some orange colored solid material precipitated out. An additional 10 ml of toluene was added to the mixture and mixed. Solid precipitate was collected with a fitted disc funnel. The solid cake was thoroughly rinsed with toluene and the solid material was allowed to air dry under vacuum. About 0.555 g of the solid compound of general formula (III) was obtained.

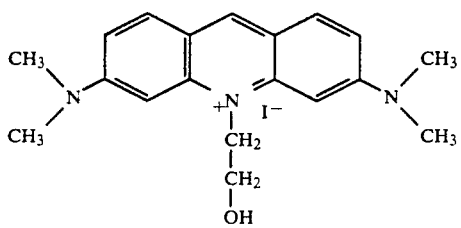

In the examples which follow, compounds of this general formula are referred to as Derivative (III); AO-10-CH$_2$CH$_2$OH

EXAMPLE 4

Characterization of the Derivative (II) Family and Derivative (III)

A. Thin Layer Chromatography - Silica gel TLC were used to identify the compounds. A mixed solvent system composed of CHCl$_3$/MeOH/H$_2$O with mol ratio of 7.5/2.5/0.3 was used. Acridine orange appeared at Rf approximately 0.50 while all of the Derivative (II) Family appeared at Rf 0.57. Derivative (III) showed a similar Rf at 0.57.

B. The $^1$H NMR spectra of Derivative (IIa) and Derivative (III) were determined on a Varian EM-360MHZ Nuclear Magnetic Resonance spectrometer following established protocols. The spectra are shown in FIG. 1a (60MHz) and FIG. 1b (60MHz) respectively. Characteristic bands of benzyl protons and ethylene protons are clearly visible. Similar spectra of Derivatives (IIb), (IIc) and (IId) were also obtained.

C. The optical absorption spectra were determined on a Perkin-Elmer Lambda 3B UV/VIS spectrophotometer. 3 ml of 3 μg/ml concentration of the subject dye derivative (Derivative (IIa)) in PBS buffer (Sigma Cat. #1000-3) was measured, and the absorption spectra of the dye compositions compared with that of acridine orange. Both of the compounds show a dimer peak near 470 nm, the monomer peak of Derivative (IIa) appears at 496 nm and that of acridine orange at 490 nm. The absorption spectra of Derivative (III) and of the other benzyl derivatives are very similar to that of Derivative (IIa). Table 1 summarizes the absorption maxima of all derivatives in this invention compared to that of acridine orange.

TABLE 1

| Absorption Maxima of Various Dyes in PBS Buffer | | |
|---|---|---|
| Compound | Monomer Abs. (nm) | Dimer Abs. (nm) |
| Acridine Orange | 490 | 470 |
| Derivative (IIa) | 496 | 470 |
| Derivative (IIb) | 495 | 470 |
| Derivative (IIc) | 497 | 470 |
| Derivative (IId) | 497 | 470 |
| Derivative (III) | 495 | 470 |

D. The fluorescence spectrum of Derivative (IIa) (see FIG. 3a) showed an emission peak at 527 nm as compared to that of acridine orange (FIG. 3b) at 533 nm when excited at 488 nm. A Hitachi F-4010 fluorescence spectrophotometer was used, with 3 ml of 1 μg/ml of the subject dye derivative in PBS buffer.

EXAMPLE 5;

pH titration of the Derivative (II) Family and Derivative (III).

Optical absorption and fluorescence spectra of the compounds at various pHs were measured. A novel buffer solution was developed for use with the derivatives, and included 1.25 mg/ml of paraformaldehyde and 9 g/l potassium oxalate. Thus buffer solution was pH adjusted by adding either small quantities of 1.0 N HCl solution or 1.0 N NaOH solution until pHs of 3.0, 5.0, 7.0, 9.0 and 12.0 were obtained. As illustrated in FIG. 2a, the absorption spectrum of Derivative (IIa) stays constant from pH 3.0 to pH 9.0 with a small decrease at pH 12.0, whereas the absorption spectrum of acridine orange (FIG. 2b) clearly changes substantially for pH 12 as is expected from the difference between tertiary and quaternary amines. Similar results were also observed for the fluorescence spectra of both compounds (See FIGS. 3a and 3b, respectively). FIG. 4b shows the pH titration curves of Derivatives (IIb) and (III). It also indicates the better stability of Derivative (II) Family and Derivative (III) at high pH when compared with acridine orange.

EXAMPLE 6

Fluorescence binding of the Derivative (II) Family and Derivative (III) to RNA (Saturated Solution)

Various volumes of RNA solution (Calbiochem Cat. No. 557112) with concentrations of 100 mg/ml in PBS buffer were added and mixed with 3 ml of the subject dye derivative solution (1g/ml dye concentration). The fluorescence spectrum of each was recorded until the dye solution was saturated with RNA. This was found to occur when 40 μl or greater volume of RNA solution was added to the dye solution.

Table 2 below shows the metachromatic fluorescence shift and fluorescence enhancement factor for the subject dye compositions as compared to acridine orange. The data demonstrates a greater shift for the invention compounds than acridine orange as well as the same or greater increase in fluorescence signal when bound to RNA. The ratio of the fluorescence signal of the bound dye to that of the free dye in solution is referred to as the Fluorescence Enhancement Factor.

TABLE 2

| Dye | Metachromatic Shift (nm) | Fluorescence Enhancement Factor |
|---|---|---|
| Acridine Orange | 1.0 | 2.2 |
| Derivative (IIa) | 3.6 | 2.2 |
| Derivative (IIb) | 3.2 | 2.3 |
| Derivative (IIc) | 5.0 | 2.7 |
| Derivative (IId) | 3.8 | 2.3 |
| Derivative (III) | 3.6 | 3.0 |

EXAMPLE 7

Microscopic examination of reticulocyte staining with the Derivative (II) Family and Derivative (III)

Protocol for sample preparation: About 20 μl of the subject derivative dye solution (stock solution of 0.3 mg/ml to 0.9 mg/ml of the compound in 100% methanol) was added to 2 ml of a buffer solution including 0.9% potassium oxalate and 1.25 mg/ml paraformaldehyde and mixed thoroughly. To this solution, 20 μl of either normal or patient blood sample was added, vortexed and held at room temperature for three minutes. The samples were then ready for reticulocyte detection. For enriched reticulocyte samples, 10 μl of blood was suspended in the 2 ml reagent. For acridine orange staining solution (used for comparison), the stock solution contained 3 mg/ml acridine orange.

For samples stained with NMB (New Methylene Blue), the National Committee for Clinical Laboratory Standards (NCCLS) protocol was followed.

The effect of variations in benzyl ring structure and nature of benzyl ring substituent were examined. For each compound, the percentage of reticulocyte counts using a Spectrum III flow cytometer distributed by Ortho Diagnostics Systems, Inc. following the manufacturer's protocols was compared with the percentage reticulocyte counts determined by microscopic examination. Table 3 below summarizes the results.

TABLE 3

| Reticulocyte Staining and Quantification with Various Dyes | | | |
|---|---|---|---|
| | | Microscopic Staining | Spectrum III (% ratio) |
| Dye | Conc. (μM) | | Normal Blood / Patient Blood |
| NMB | NCCLS | + | 1.7% (NCCLS) / 5.3% (NCCLS) |
| AO | 100 | + | NM / NM |
| Derivative (IIa) | 7 | + | 2.21 / 5.0 |
| Derivative (IIb) | 7 | + | 1.5 / 5.9 |
| Derivative (IIc) | 7 | + | 2.1 / NM |
| Derivative (IId) | 7 | + | 1.8 / NM |
| Derivative (III) | 7 | + | 1.5 / 5.6 |
| AO-2-NO$_2$-Benzyl | 8 | − | ND / ND |
| AO-2-Chloro-Benzyl | 8 | − | ND / ND |

NM = Not Measured
ND = Non-Detectable

Further experimentation has shown that the derivatives of the present invention are effective at a concentration as low as 2 μM, although, stronger staining is seen at a concentration of 7 μM.

Under the microscope, reticulocytes which showed red precipitates of RNA were clearly observed for those blood samples stained with Derivative (IIa), (IIb), (IIc), (IId) and (III). However, acridine orange-10-2-nitro-benzyl and acridine orange-10-2-chloro-benzyl did not stain the reticulocytes specifically. In this study, acridine orange was used as a reference to show that not all substitutes at the benzyl hydrogen can stain reticulocytes. It was noticed that the amount of acridine orange needed for good reticulocyte staining was about 10–14 times higher than the amount needed of Derivative (II) or (III).

EXAMPLE 8;

Stability of the reagent performance within days using Derivative (IIa)

In order to develop a cytometric method for reticulocyte counting, it is desirable that the reagent employed for the measurement give a reproducible result in one working day. For evaluation, a reagent containing Derivative (IIa) was compared with one containing acridine orange. One blood sample (normal) was stained with the dye solutions separately. The protocol for the sample preparation was as described for Example 7. A Spectrum III flow cytometer was used for this evaluation. After blood was added to the dye solutions, the two different mixtures were left at room temperature and exposed to ambient light. Reticulocyte counting of the two mixtures was conducted at different time intervals for up to eight hours. At each interval, the measurement was run in duplicate. Table 4 below summarizes the results.

TABLE 4

| Reproducibility of Reagent at Room Temperature | | |
|---|---|---|
| | % Reticulocyte Counts | |
| Time Elapsed | AO (100 uM) | Derivative (IIa) (7 uM) |
| 5 min | 1.5, 1.2 | 1.1, 1.0 |
| 10 min | — | 1.0, 1.1 |
| 30 min | 1.3, 1.6 | 1.2, 1.2 |
| 60 min | 1.2, 1.2 | 1.2, 1.0 |
| 2 hr | 1.3, 1.4 | 1.1, 1.0 |
| 3 hr | 1.5, 1.3 | 1.1, 1.1 |
| 4 hr | 1.2, 1.6 | 1.1, 1.3 |
| 5 hr | 1.1, 1.6 | 1.3, 1.1 |
| 6 hr | 1.9, 1.4 | 1.0 |

TABLE 4-continued

Reproducibility of Reagent at Room Temperature

| | % Reticulocyte Counts | |
|---|---|---|
| Time Elapsed | AO (100 uM) | Derivative (IIa) (7 uM) |
| 7 hr | 1.8, 1.4 | 1.0, 1.0, 1.2 |
| 8 hr | 1.4, 1.4 | 1.0, 1.4 |
| Mean | 1.4% | 1.12% |
| S.D. | 0.23% | 0.12% |
| % CV | 16% | 10.7% |

It is apparent that Derivative (IIa) gives more reproducible counts in eight hours. The 10.7% CV for Derivative (IIa) is to be compared with 16% CV for acridine orange.

Given the similarities in chemical structure among the other Derivative (II) Family and Derivative (III), similar stability results would be expected.

EXAMPLE 9

Stability of the reagents (shelf life)

Figure 5B:
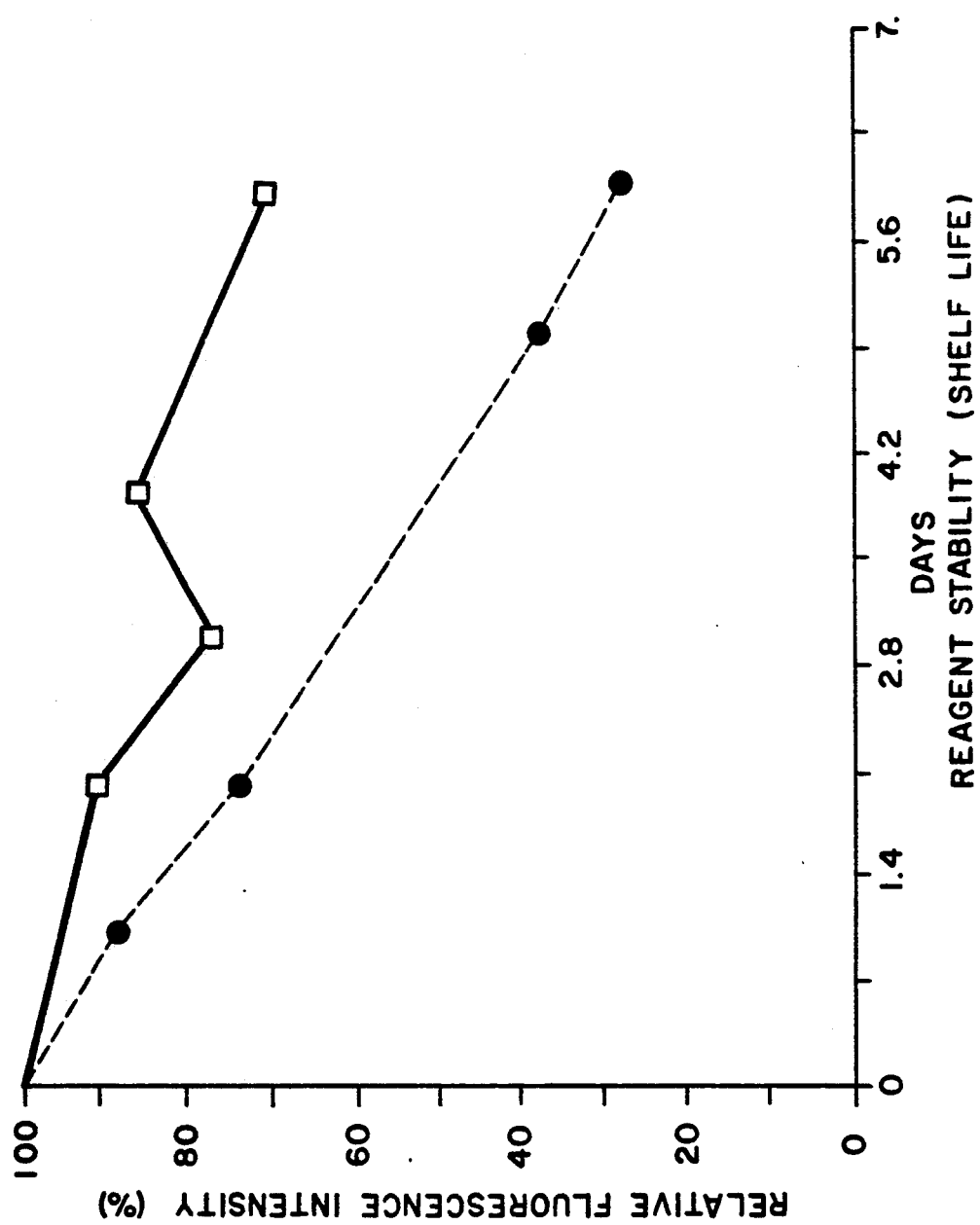

The stabilities of two reagents were studied and compared. 3 ug/ml concentration of Derivative (IIa) and 30 μg/ml of acridine orange each in the buffer solution of Example 7 were left at room temperature unprotected from ambient light for a week. The absorption and fluorescent spectra of the dye solutions were recorded each day. Intensities at absorption maxima for acridine orange (λ490 nm) and for Derivative (IIa) (λ495 nm) and fluorescence maxima for acridine orange (λ533 nm) and for Derivative (IIa) (λ527 nm) were measured and compared to those of the freshly prepared dye solutions containing Derivative (IIa) and acridine orange, respectively at Day 0. The % decrease in intensity each day was plotted as a function of time (i.e. days). FIGS. 5a and 5b display the changes in absorption and fluorescence separately. It is clear that the reagent containing Derivative (IIa) has the least drop in both fluorescence and absorption intensities after six days. About 30% decrease in both fluorescence and absorption was observed for the benzyl derivative and 70% decrease for acridine orange. Thus, Derivative (IIa) is more stable and gives more reproducible reticulocyte counts than acridine orange.

Given the similarities in chemical structure among the other Derivative (II) Family and Derivative (III), similar stability results would be expected for these derivatives.

EXAMPLE 10

Correlation study with NCCL's manual reference method.

Figure 6A:
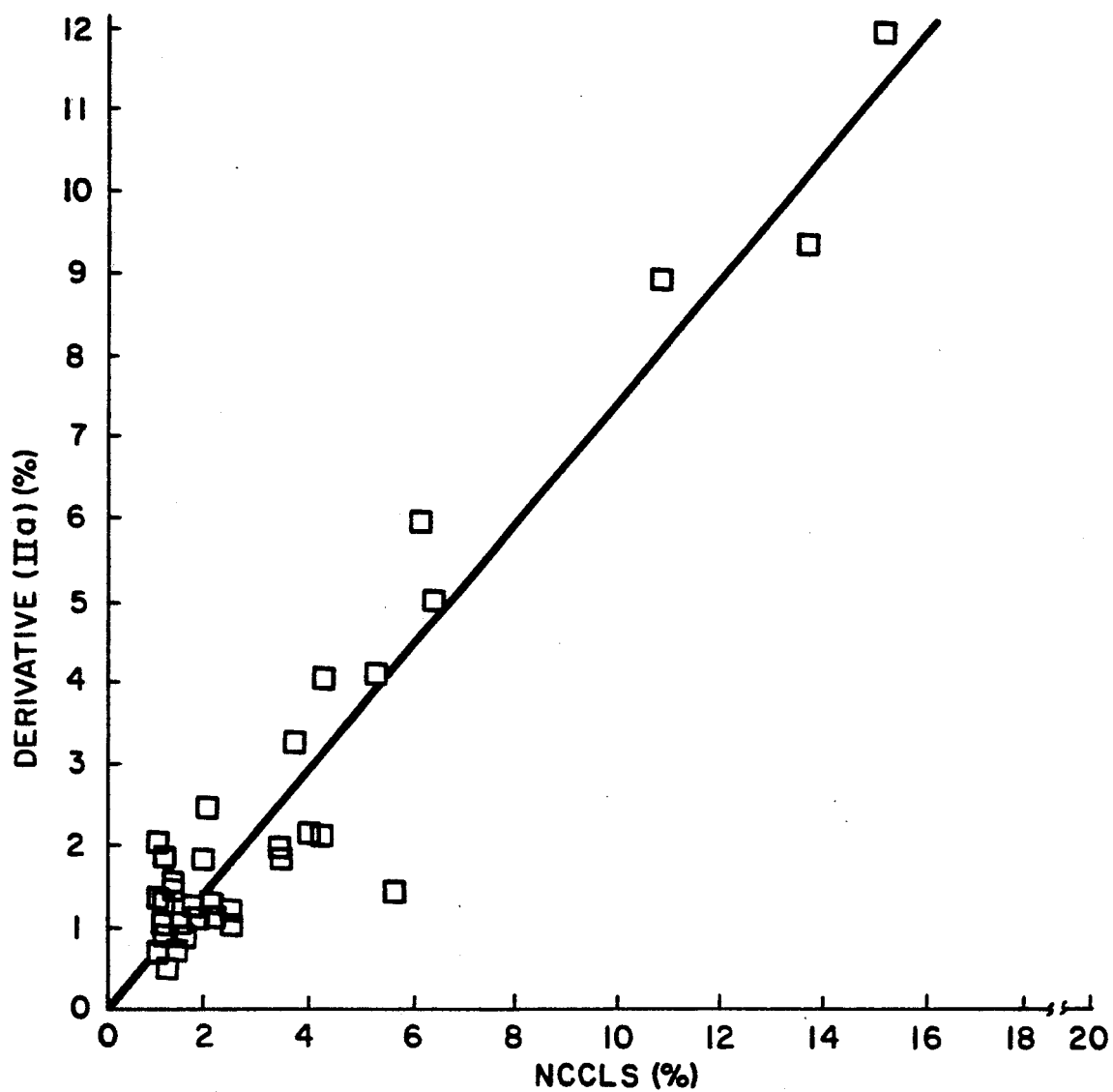
FIGS. 6a and 6b are correlation data for analysis using Derivative (IIa) at different concentrations in a commercial automated method as compared with NCCL's approved manual method.
Figure 6B:
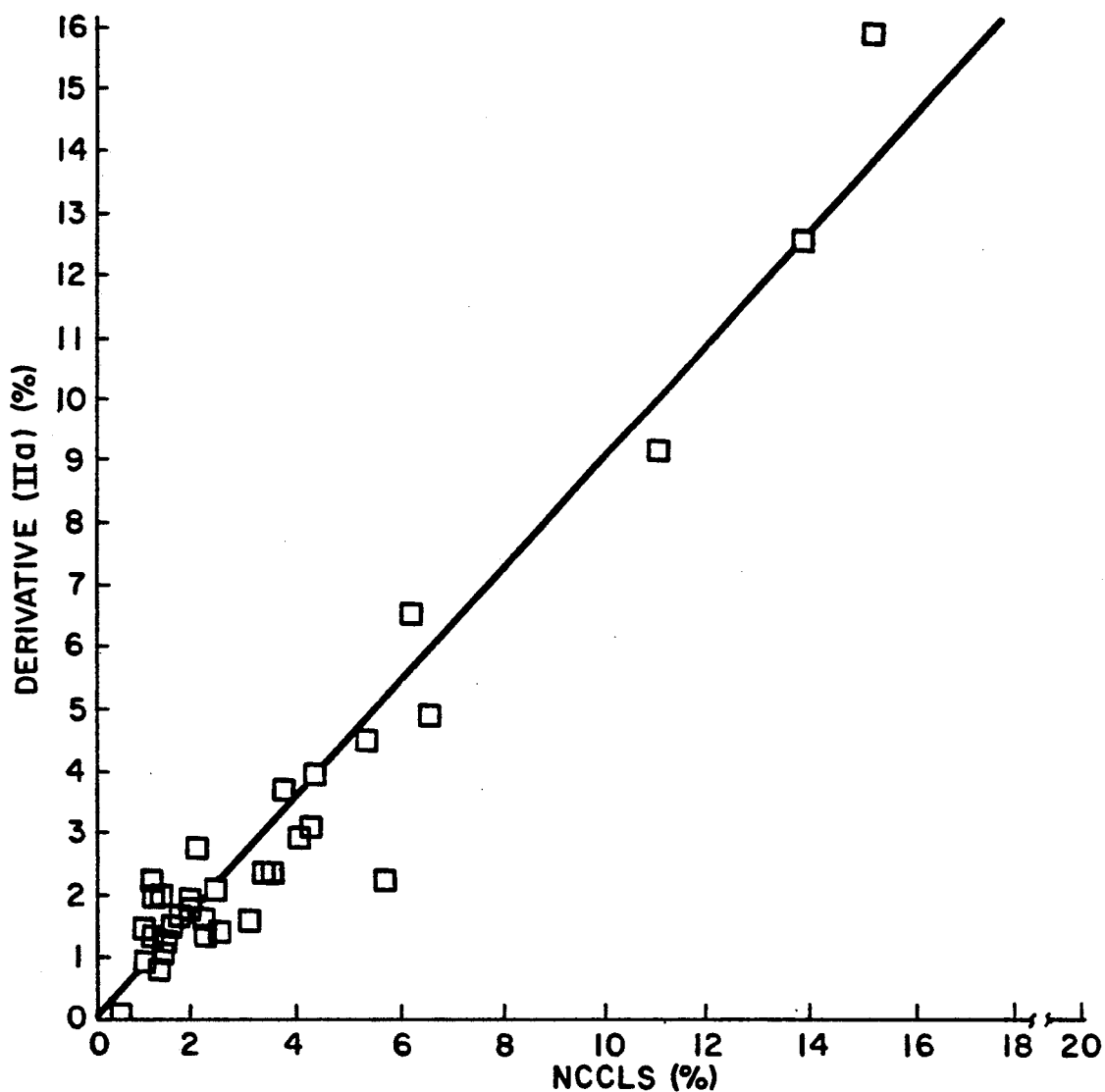

A study to compare the performance of Derivative (IIa) and Derivative (III) when used in a dye reagent in an automated method with the NCCL's manual method was conducted. The Spectrum III system was used for this study, and the sample protocol as described in Example 7 for the Spectrum III instrument was followed. Forty-three blood samples, including 31 normals, 8 abnormals and 4 reticulocyte enriched samples were stained with a reagent containing the subject dye derivative and assayed for their reticulocyte contents. Reticulocytes in the same set of blood samples were also counted using the NCCL's approved manual method. The percentage reticulocyte counts obtained from these two methods are compared in FIGS. 6a and 6b. At as low as 3 mg/ml (or 7 μM) concentration of Derivative (IIa) in the reagent, good correlation data are obtained, i.e. correlation coefficient 0.96, slope 0.71 and intercept 0% (see FIG. 6a). At 9 μg/ml (or 21 μM) concentration, the correlation of the reagent of our invention vs. the reference method is also very good (see FIG. 6b). A correlation coefficient of 0.97, slope of 0.87 and intercept of 0% are comparable to that of the 3 μg/ml.

Figure 7:
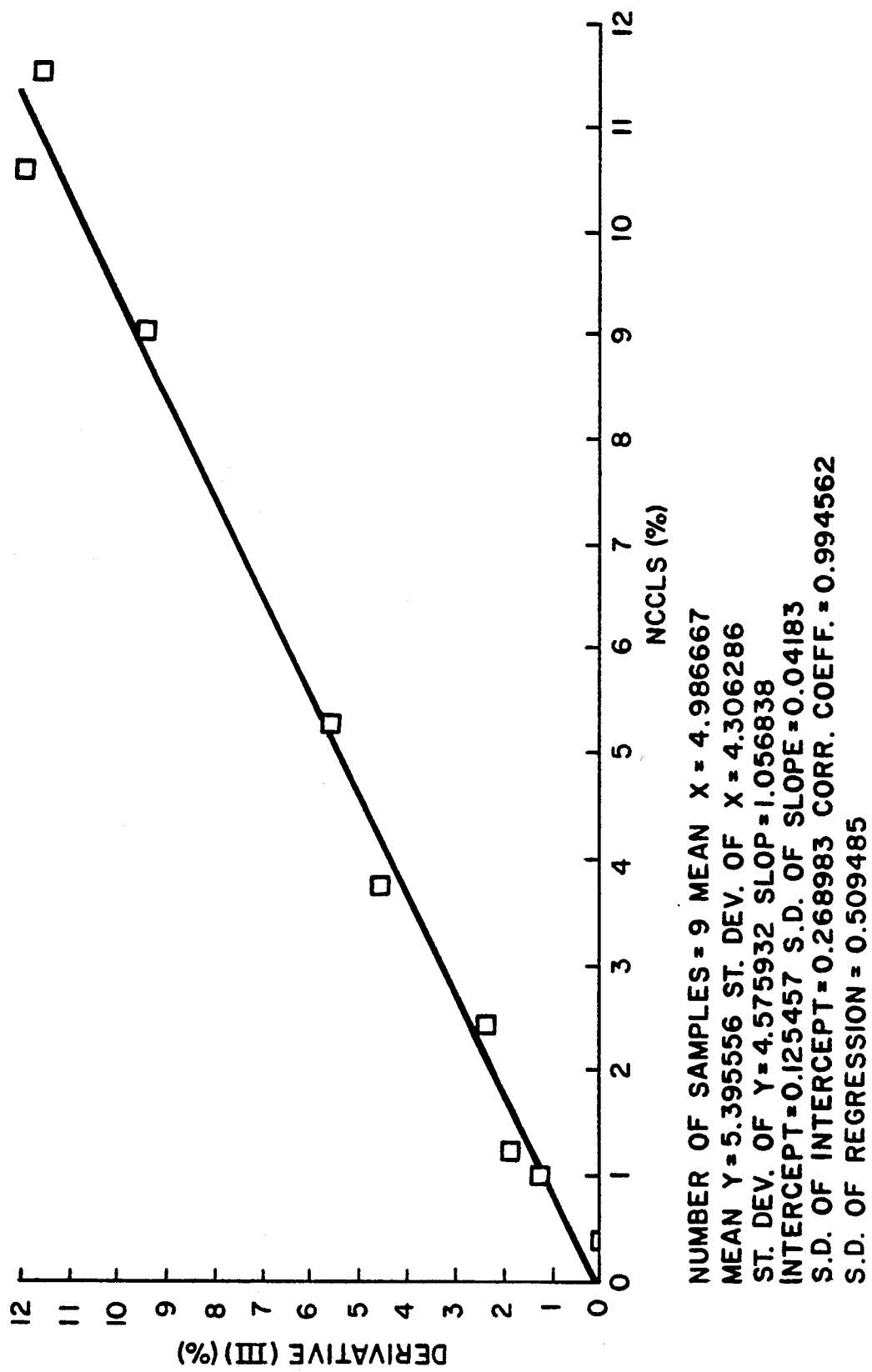
FIG. 7 is the correlation data for Derivative (III)

For Derivative (III), FIG. 7 shows a correlation coefficient of 0.99 and a slope of 1.06 and intercept of 0.13% based on a nine patient sample.

EXAMPLE 11

Correlation with a commercial automated cytometric method.

The protocols of Example 8 were followed for all sample measurements using the Spectrum III system.

Figure 8A:
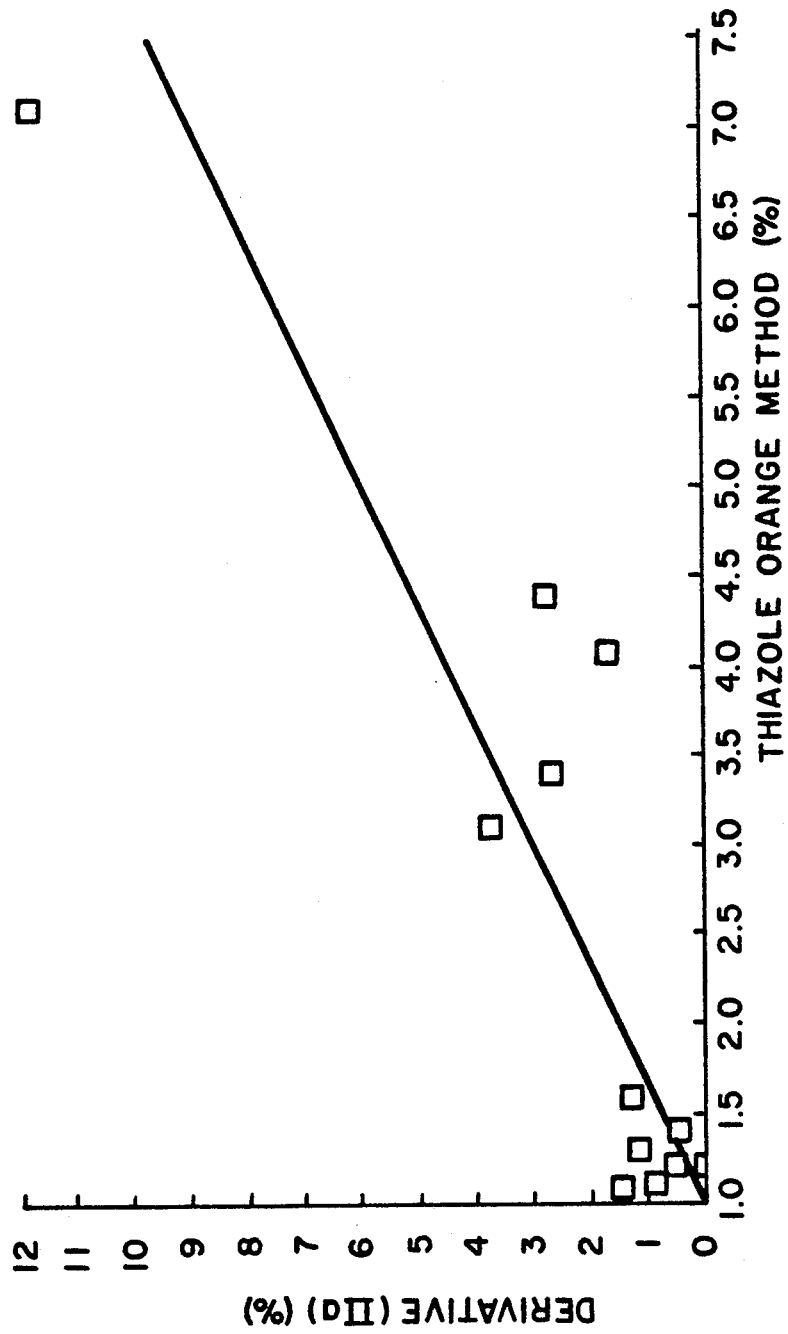
FIGS. 8a and 8b are the correlation data of Derivatives (IIa) and (III) in a commercial automated method as compared with another commercial automated method using thiazole orange.

Twelve patient samples obtained from various patients were measured for their reticulocyte counts simultaneously employing the two different flow cytometric methods. The above reagent at 6 μg/ml concentration of Derivative (IIa) using the Spectrum III vs. the B-D FACScan method using thiazole orange. The B-D method requires incubation of the blood sample with the thiazole orange reagent for a minimum of 30 minutes in the dark. By comparison, our claimed reagent can provide accurate reticulocyte counts within three minutes in the room light. Each measurement was carried out in duplicate. Good correlation was obtained. FIG. 8a shows the result: correlation coefficient 0.88, slope 1.45 and intercept −1.4%. Since the B-D FACScan method is a commercialized cytometric method, these results indicate comparability of the claimed reagent to the recognized cytometric counting method.

Figure 8B:
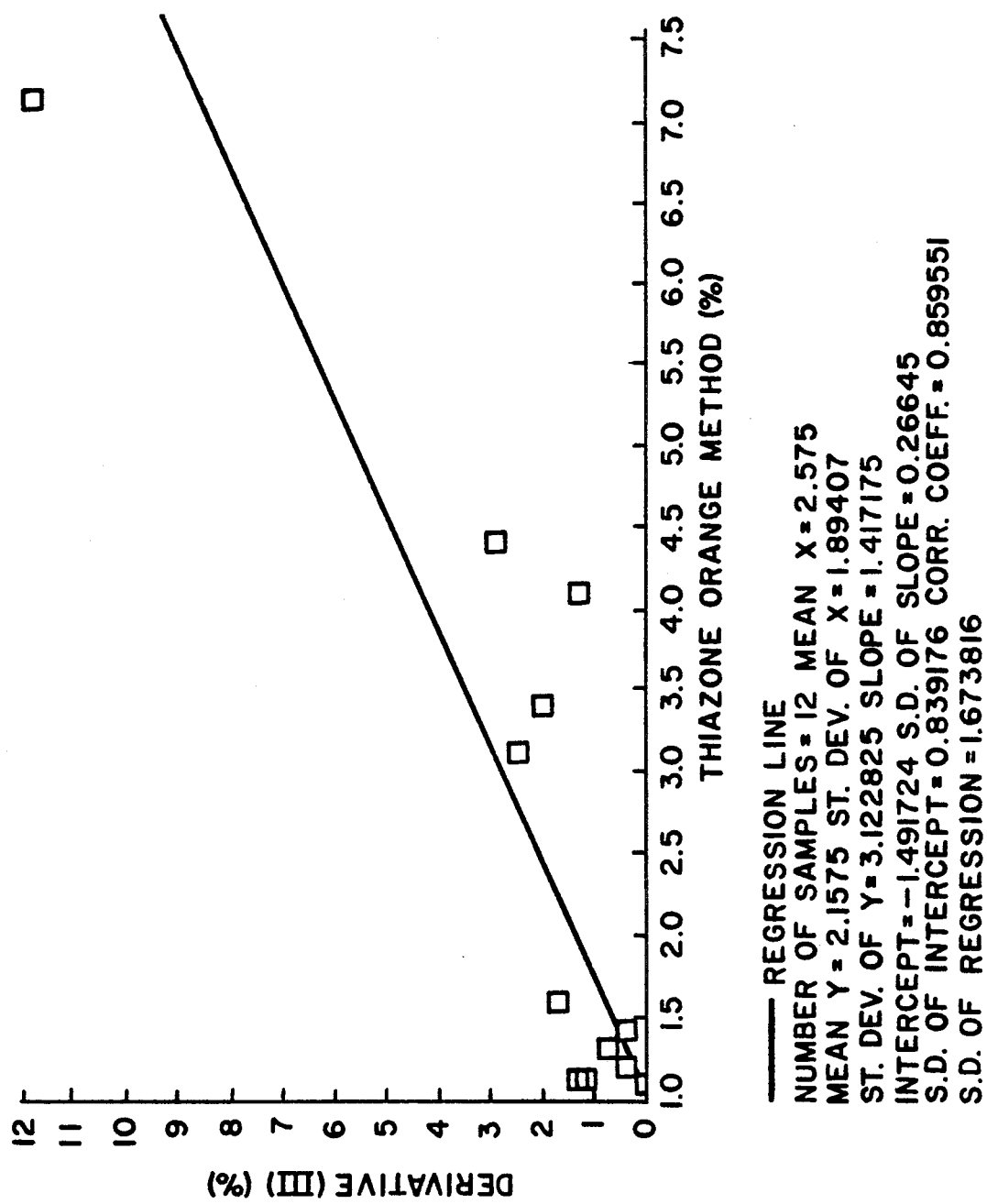

Twelve patient samples were mixed with 6 μg/ml concentration of a reagent containing Derivative (III) following the above protocol and the data are illustrated in FIG. 8b.

EXAMPLE 12

Figure 9:
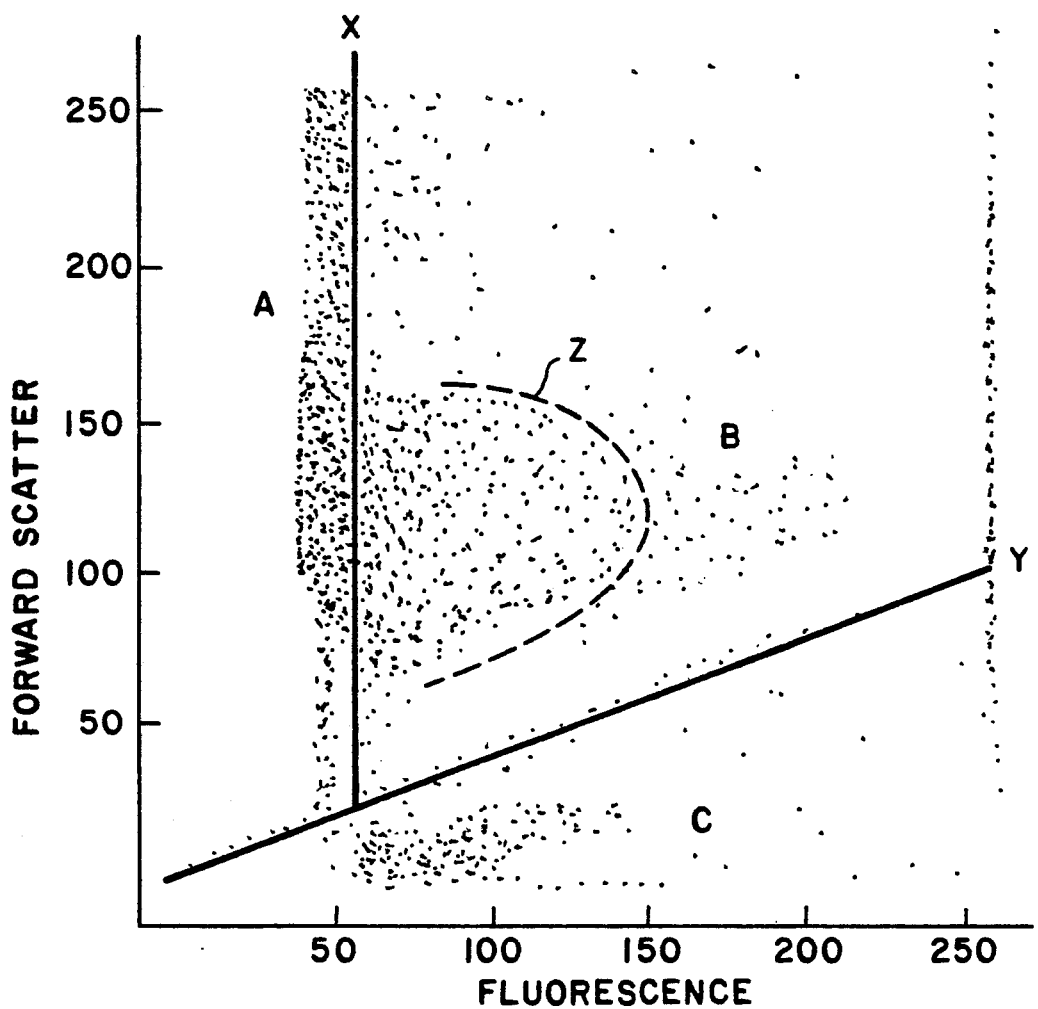
FIG. 9 is a cytogram of forward scatter vs. fluorescence for reticulocytes stained with Derivative (III).

FIG. 9 demonstrates the high degree of discrimination between reticulocyte and erythrocyte populations when cells were stained with Derivative (III), and measured by the Spectrum III instrument. The sample preparation protocol is the same as discussed above. Distinct cell populations were clearly observed based on their particular scatter and fluorescence signals. The erythrocyte population falls within Region A between the vertical axis and vertical line X. These cells show high scatter signals and low cell fluorescence signals. The reticulocyte population falls within Region B (to the right of X). These cells are distinguishable from the erythrocytes due to the high fluorescence signals from their Derivative (III) stained RNA. The platelet population lies within Region C below line Y. These cells have relatively low scatter signals and fluorescence signals when compared to the reticulocytes. The parabolic like boundary line Z in Region B represents the extent of fluorescence signal that would be obtained if acridine orange were used as the stain rather than Derivative (III). Thus, it is readily apparent that by using Derivative (III), a greater sensitivity is achieved since the ratio of the fluorescence signal of the reticulocytes to the erythrocyte fluorescence signal is high for the Derivative (III) stained cells than for those stained with acridine orange.

Based on the fluorescence separation between erythrocytes and reticulocytes, the reticulocyte count of a patient sample was measured to be 2.2%. The same blood sample was also analyzed by the NCCLS method. The result was a reticulocyte count of 2.6%.

Some advantages of the present invention evident from the foregoing description include an improved dye composition and reagents incorporating such composition for the quantitative determination of reticulocytes in whole blood. The dye consists of special structures of quaternized derivatives of acridine orange proven to be more stable chemically and to provide greater reproducibility of reticulocyte counts when compared to dyes previously used.

In view of the above, it will be seen that the various objects of our invention are achieved and other advantageous results attained.

The various features and advantages of the invention are thought to be clear from the foregoing description. However, various other features and advantages not specifically enumerated will undoubtedly occur to those versed in the art, as likewise will many variations and modifications of the preferred embodiments illustrated, all of which may be achieved without departing from the spirit and scope of the invention as defined by the following claims.

We claim:

1. A quaternized derivative of acridine orange of the formula:

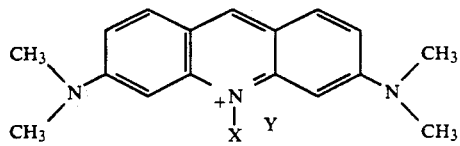

wherein Y is bromide (Br−) or iodide (I−), and wherein X is the R₁ and/or R₂ substituted benzyl group

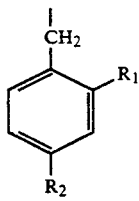

wherein R₁ is hydrogen or fluorine, and R₂ is fluorine, trifluoromethyl or hydrogen, except R₁ and R₂ cannot both by hydrogen.

2. A reagent for staining reticulocytes in a whole blood sample for quantitation which reagent is characterized in that it includes an aqueous solution of:
   a) a quaternized derivative of acridine orange of the formula:

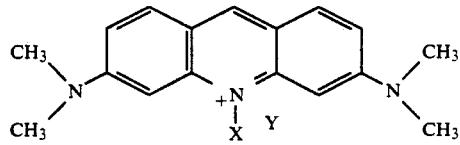

wherein Y is bromide (Br−) or iodide (I−), and X may be R₁ and/or R₂ substituted benzyl group

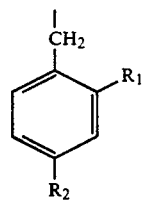

in which R₁ is hydrogen or fluorine, and R₂ is fluorine, trifluoromethyl or hydrogen, or X may be hydroxyl ethylene, and
   b) a buffer system.

3. The reagent of claim 2 wherein the buffer system maintains the pH at about 7.0.

4. The reagent of claim 2 wherein the buffer system comprises paraformaldehyde and potassium oxalate.

5. The reagent of claim 4 wherein said paraformaldehyde is present at a concentration of about 1.25 g/L and said potassium oxalate is present at a concentration of about 9 g/L.

6. The reagent of claim 2 wherein said quaternized derivative of acridine orange is present at a concentration of from about 2 μM to about 20 μM.

7. The reagent of claim 6 wherein said quaternized derivative of acridine orange is present at a concentration of about 7 μM.

8. A method for quantitating reticulocytes in a whole blood sample by flow cytometry which comprises the steps of:
   (a) mixing a sample of blood to be tested with a reagent comprising an aqueous solution of the quaternized derivative of acridine orange of the formula:

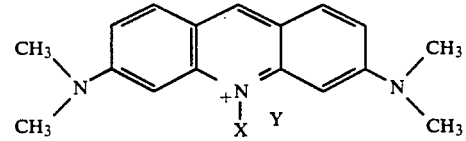

wherein Y is bromide (Br−) or iodide (I−), and X is the R₁ and/or R₂ substituted benzyl group

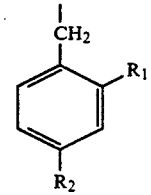

in which R₁ is hydrogen or fluorine, and R₂ is fluorine, trifluoromethyl or hydrogen, or X is hydroxyl ethylene, to form a suspension;
   (b) allowing the suspension to react for a sufficient time so that the derivative is effectively taken up by the reticulocytes;
   (c) exposing the suspension to radiation from a blue laser light source;
   (d) measuring the intensity of orange fluorescence from the suspension; and
   (e) determining the amount or percentage of reticulocytes in the sample from said measurement.

9. The method of claim 8 wherein the reaction time in step (b) is about three minutes.

10. The method of claim 8 wherein the reagent includes a buffer system.

11. The method of claim 10 wherein the buffer system maintains the pH at about 7.0.

12. The method of claim 10 wherein the buffer system comprises paraformaldehyde and potassium oxalate.

13. The method of claim 12 wherein said paraformaldehyde is present at a concentration of about 1.25 g/L and said potassium oxalate is present at a concentration of about 9 g/L.

14. The method claim 12 wherein said quaternized derivative of acridine orange is present at a concentration of from about 2 $\mu$M to about 20 $\mu$M.

15. The method of claim 14 wherein said quaternized derivative of acridine orange is present at a concentration of about 7 $\mu$M.

* * * * *

UNITED STATES PATENT AND TRADEMARK OFFICE
CERTIFICATE OF CORRECTION

PATENT NO.   : 5,075,556
DATED        : December 24, 1991
INVENTOR(S)  : Sophie Fan and Gena Fischer It is certified that error appears in the above-identified patent and that said Letters Patent is hereby corrected as shown below:

Column 4, line 5, formula (I) should be amended to include "Y", as follows:

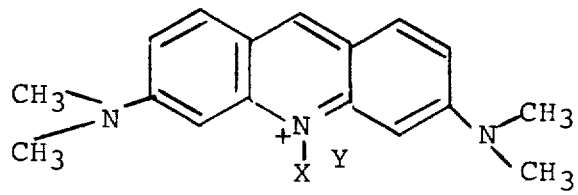

Signed and Sealed this

Thirteenth Day of April, 1993

Attest:

STEPHEN G. KUNIN

Attesting Officer

Acting Commissioner of Patents and Trademarks